(12) United States Patent
Yan et al.

(10) Patent No.: US 9,903,835 B2
(45) Date of Patent: Feb. 27, 2018

(54) FULLY AUTOMATED HIGH-PRECISION CAPILLARY ELECTROPHORESIS INSTRUMENT

(71) Applicant: Chao Yan, Shanghai (CN)

(72) Inventors: Chao Yan, Shanghai (CN); Dong Yao, Shanghai (CN); Lin Zhang, Shanghai (CN); Jing Li, Shanghai (CN)

(73) Assignee: Chao Yan, Shanghai (CN)

( * ) Notice: Subject to any disclaimer, the term of this patent is extended or adjusted under 35 U.S.C. 154(b) by 28 days.

(21) Appl. No.: 15/128,032

(22) PCT Filed: May 8, 2014

(86) PCT No.: PCT/CN2014/000473
§ 371 (c)(1),
(2) Date: Sep. 21, 2016

(87) PCT Pub. No.: WO2015/139156
PCT Pub. Date: Sep. 24, 2015

(65) Prior Publication Data
US 2017/0102359 A1    Apr. 13, 2017

(30) Foreign Application Priority Data
Mar. 21, 2014  (CN) .......................... 2014 1 0108667

(51) Int. Cl.
*G01N 27/447* (2006.01)

(52) U.S. Cl.
CPC . *G01N 27/44743* (2013.01); *G01N 27/44708* (2013.01); *G01N 27/44791* (2013.01)

(58) Field of Classification Search
CPC ...................... G01N 27/447–27/44795; B01D 57/00–57/02; C02F 1/4696; B81B 1/00–1/008
USPC ............... 204/450–470, 546–550, 600–621, 204/643–645
See application file for complete search history.

(56) References Cited

U.S. PATENT DOCUMENTS

| | | | |
|---|---|---|---|
| 6,387,234 B1 * | 5/2002 | Yeung .............. | G01N 27/44782 204/451 |
| 2009/0020429 A1 | 1/2009 | Ozawa et al. | |
| 2015/0192544 A1* | 7/2015 | Breadmore ...... | G01N 27/44743 204/550 |

FOREIGN PATENT DOCUMENTS

| | | |
|---|---|---|
| CN | 1122451 A | 5/1996 |
| CN | 2694272 Y | 4/2005 |
| CN | 1737562 A | 2/2006 |
| CN | 101561425 A | 10/2009 |

(Continued)

*Primary Examiner* — Bach T Dinh
(74) *Attorney, Agent, or Firm* — Muncy, Geissler, Olds & Lowe, P.C.

(57) ABSTRACT

A fully automated high-precision capillary electrophoresis instrument, comprising an electrophoresis system, a sample injection flow path, and an automatic sampling flow path; the sampling flow path comprising a shunt waste bottle, which is connected to a four-way connector, a four-way sample injection valve and a buffer syringe pump; the automatic sampling flow path comprises a sampling needle, a sample tray, a cleaning tank, reagent bottles, a buffer tube, a six-channel liquid dispenser, and a syringe pump. The described capillary electrophoresis instrument has a fast sample injection speed, high accuracy, good reproducibility, and can be widely used in automated analysis of different substances by capillary electrophoresis.

10 Claims, 4 Drawing Sheets

(56) References Cited

FOREIGN PATENT DOCUMENTS

| CN | 203786079 U | 8/2014 |
|---|---|---|
| EP | 1378745 A1 | 1/2004 |
| JP | 2001281221 A | 10/2001 |

* cited by examiner

FULLY AUTOMATED HIGH-PRECISION CAPILLARY ELECTROPHORESIS INSTRUMENT

TECHNICAL FIELD

The present invention is related to capillary electrophoresis, more specifically, related a fully automatic, high-precision capillary electrophoresis instrument. It belongs to the field of analytical instrumentation.

BACKGROUND OF THE INVENTION

Capillary electrophoresis (CE) was invented in the 1980s. A high-voltage is applied across a capillary filled with the electrolyte during the analysis so that charged molecules within the electrolyte move with different speed and in different direction depending on their electrophoretic mobility (namely, size to charge ratio of a compound), and therefore, are separated in the capillary. However, because the electroosmotic flow is always stronger than their electrophoretic mobility, all the compounds in the capillary are eventually carried to the detection end of the capillary and detected. Thus, the CE instrument can be used to separate charged molecules with different electrophoretic mobility.

The main components of CE include a separation capillary, two liquid containers at both ends of capillary, high voltage power supply, two electrodes, a detector and data output and processing device.

Hydrodynamic injection and electrophoretic injection are the two conventional injection approaches of CE. Electrophoretic injection injects the sample relying on electrophoretic mobility and (or) electroosmotic flow (EOF); but this injection mode results in bias for charged compounds and reduce the accuracy and reliability of the analysis. In addition, the two above injection methods have the following disadvantages: firstly, the high voltage across the capillary should be turned off during injection, making the established electric field interrupted and then re-established from time to time, resulting in poor precision of the analysis; secondly, both the two methods conduct the injection through "dip in" approach, which could cause cross contamination between sample and buffer solution or between different samples.

In short, the injection size of CE is very small even to nano-liter level, the traditional CE injection methods are unable to inject such small amount sample accurately. And the injection through "dip in" approach brings very poor repeatability, which makes it very difficult to achieve quota-sampling.

SUMMARY OF THE INVENTION

A technical problem to be solved by the present invention is to overcome defects of the prior art and provide a fully automated high-precision capillary electrophoresis instrument so as to implement automatic quantitative sample injection, improve the accuracy and precision (reproducibility) of sample injection, eliminate cross contamination and electric bias, increase the sample injection speed, shorten the sample injection time, prevent outside air from entering a sample injection fluid path, and also realize automatic cleaning and balancing of different reagents to capillary separation columns.

A scheme provided by the present invention to solve the technical problem is as follows:

A fully automated high-precision capillary electrophoresis instrument includes an electrophoresis system. The electrophoresis system includes an electrophoretic separation capillary, a column thermostat and an detector, wherein the outlet of the electrophoretic separation capillary is inserted into a buffer solution outlet bottle, the column thermostat and the ultraviolet detector are successively connected with the electrophoretic separation capillary, one electrode of a high-voltage power supply is inserted into the buffer solution outlet bottle, the other electrode of the high-voltage power supply is connected with the electrophoretic separation capillary by an electrical decoupler, and a high-voltage electric field is applied across the electrophoretic separation capillary. The fully automated high-precision capillary electrophoresis instrument is characterized:

The capillary electrophoresis instrument further includes a sample injection flow path connected with the electrophoresis system and an automatic sampling flow path connected with the sample injection flow path;

The sample injection flow path includes a shunt waste bottle, a four-way sample injection valve and a buffer syringe pump respectively connected to three ports of a four-way connector;

The four-way sample injection valve, which is used for quantitatively injecting sample to the electrophoretic separation capillary, includes four fixed ports, namely, an S port, a W port, a P port and a C port, and also includes a rotatable built-in quantitative loop, wherein the C port is connected with the electrophoretic separation capillary, the P port is connected with the four-way connector, the built-in quantitative loop is provided with a bypass-flow path and a quantitative flow path having a constant volume; as the built-in quantitative loop rotates, the bypass-flow path and the quantitative flow path switch between connecting the S port and the W port and connecting the P port and the C port;

The automatic sampling flow path includes of the sampling needle, cleaning liquid bottle, reagent bottle as well as a six-channel liquid dispenser and a syringe pump which are connected by two ends of a buffer tube;

The syringe pump is provided with a three dispensing valve whose three ports respectively connect with the cleaning liquid bottle, autosampler waste bottle and the buffer tube. The three dispensing valve can switch the functions of exhausting and cleaning;

The six-channel liquid dispenser is provided with a fixed port and six dispensing ports which can be connected alternately with the fixed port. The fixed port is connected with the buffer tube, and the six distributing ports are respectively connected with the sampling needle, one port of a four-way connector, a S port of a four-way sample injection valve and three reagent bottles with different reagents for cleaning and balancing the electrophoretic capillary;

There is a cleaning tank for cleaning the sampling needle between the cleaning liquid bottle and the autosampler waste bottle. And the sampling needle can switch between the cleaning tank and the sample tray with different samples.

The autosampler waste bottle was connected to the W port of the said four-way sample injection valve.

As a further improvement, the electrophoresis system includes balance waste liquid bottle. The outlet of the electrophoretic separation capillary could switch between the balance waste liquid bottle and the buffer solution outlet bottle.

As a further improvement, the quantitative path of the four-way sample injection valve has volume between 1 nL to 20 nL.

As a further improvement, a capillary pressure sensor is provided to connect the buffer syringe pump and the four-way connector and to detect a working pressure of tubes. A sampling flow pressure sensor is provided between the three dispensing valve of the syringe pump and buffer tube, to detect the working pressure of sampling flow path.

As a further improvement, the sample tray has a constant temperature structure and a cooling structure.

As a further improvement, the described cleaning liquid bottle contains cleaning liquid which should be ethanol or deionized water.

As a further improvement, the functions of all the capillary electrophoresis components can achieve the automation by a computer program.

As a further improvement, the four-way connector and shunt waste bottle were connected with a shunt tube, which can balance the internal pressure of capillary electrophoresis.

As a further improvement, the detector should be UV detector on the columns or other kinds of detectors on the columns.

Compared with the traditional CE apparatus, this invention features an automatic sampling flow path that combines a syringe pump (with a three dispensing valve) and a six-channel liquid dispenser. Via this path, the sample is first rapidly pumped into the buffer tube between the syringe pump and the liquid dispenser, then pumped into a four-way sample injection valve with positive pressure by switching the passageway of the six-channel liquid dispenser. Such a process overcomes the many defects of negative pressure sampling, such as slow injection, helps to greatly reduce the injection time needed while preventing the external air from entering into the sample injection flow path. It also substantially improves the accuracy and precision of sample injection, achieves self-cleaning and balancing of different reagents on the capillary separation column, and eliminates electrical bias and the cross contamination between samples. In addition, the present invention adopts a four-way sample injection valve with a built-in quantitative loop whose quantificational volume could be between 1 nL to 20 nL. The sampling mode in this invention has overcome the defects that unable to accurately and precisely achieve such a small sample size, brought from the traditional injection with "dip in" approach.

The mentioned fully automated high-precision capillary electrophoresis instrument in this invention have the advantages of high injection speed, high accuracy, high precision and good reproducibility and easy to commercialize. Furthermore, the automation of sample injection, capillary cleaning and balancing have been achieved so that the instrument could be widely used to conduct capillary electrophoresis analysis for different substances.

1. buffer syringe pump, 2. capillary pressure sensor, 3. four-way connector, 4. shunt waste bottle, 5. four-way sample injection valve, 6. electrical decoupler, 7. electrophoretic separation capillary, 8. column thermostat, 9. high voltage power supply, 10. ultraviolet detector, 11. buffer solution outlet bottle, 12. balance waste liquid bottle, 13. six-channel liquid dispenser, 14. buffer tube, 15. sampling needle, 16. sample tray, 17. cleaning tank, 18. sampling flow pressure sensor, 19. syringe pump, 20. reagent bottle, 21. cleaning liquid bottle, 22. autosampler waste bottle, 51. quantitative flow path, 52. bypass-slow path.

DETAILED DESCRIPTION OF THE INVENTION

Below in conjunction with the accompanying drawings and specific embodiments of the present invention will be described in detail, but the following examples are not limited to the scope of the present invention, where the equivalent variations and modifications made in accordance with the contents of this description, should belong to the claimed invention of the present patent application.

The fully automated high-precision capillary electrophoresis instrument described in the present invention is used to conduct capillary electrophoresis analysis for different substances.

Figure 1:
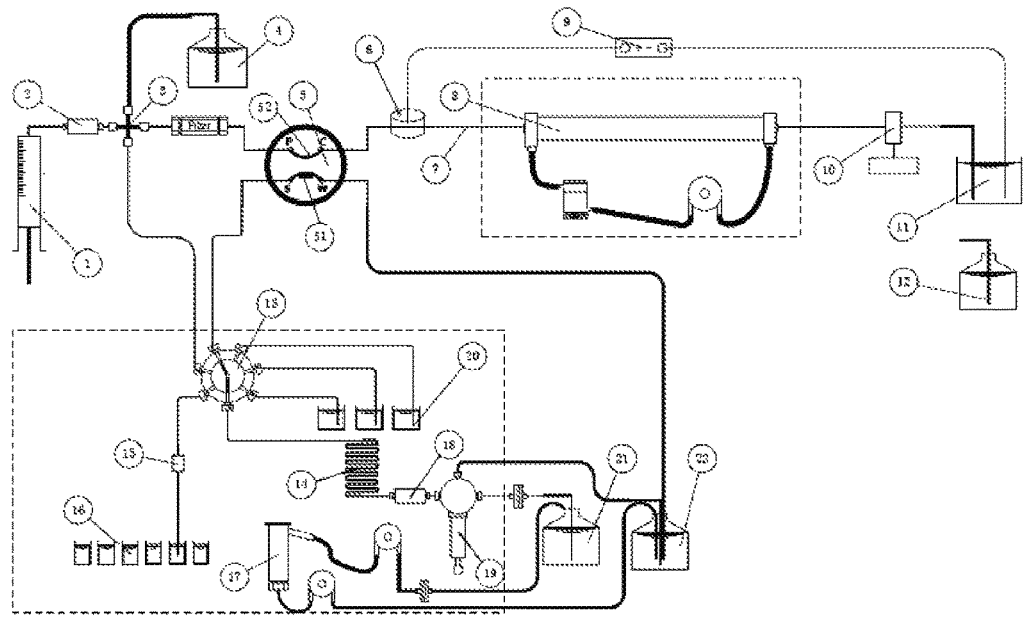
FIG. 1 is a schematic diagram of the structure of the present invention.

As shown in FIG. 1, the fully automated high-precision capillary electrophoresis instrument includes the electrophoresis system, sample injection flow path connected to the electrophoresis system and automatic sampling flow path connected to the sample injection flow path.

The described electrophoresis system includes an electrophoretic separation capillary 7, a column thermostat 8, a ultraviolet detector 10, high voltage power supply 9, electrical decoupler 6, buffer solution outlet bottle 11 and balance waste liquid bottle 12. The electrophoretic separation capillary 7 is the place for separating substances and is also the core component for separating of this system and its outlet is inserted into a buffer solution outlet bottle. The column thermostat 8 is to dissipate the joule heat generated by the electric current in the electrophoresis separation capillary and the UV detector 10 is used to detect the sample component after separation. The described column thermostat 8 and UV detector 10 are successively connected to the electrophoretic separation capillary 7. The buffer solution outlet bottle is outlet of the electrophoretic separation capillary 7 during the process of capillary electrophoresis analysis and one electrode of the high voltage power supply 9 is insert into the buffer solution outlet bottle and the other electrode is connected to the electrophoretic separation capillary 7 through the electrical decoupler 6 so that the electric field can be formed across the electrophoretic separation capillary 7. The outlet of electrophoretic separation capillary 7 can be switched between the buffer solution outlet bottle 11 and balance waste liquid bottle 12. When cleaning or balancing the electrophoretic separation capillary 7, its outlet should be switch into balance waste liquid bottle 12, or the result of measurement would be affected because of the changed buffer PH value in the buffer solution outlet bottle 11.

The injection flow path includes a buffer syringe pump 1, a capillary pressure sensor 2, a four-way sample injection valve 5, a shunt waste bottle 4 and a four-way connector 3. The buffer syringe pump 1 is used to supply buffer and support certain pressure for the electrophoretic separation capillary 7. The capillary pressure sensor 2 can detect the working pressure of electrophoretic separation capillary 7 and bypass-slow path, and the shunt waste bottle 4 can accommodate the buffer discharged from the four-way connector 3.

The four-way sample injection valve 5 has four fixed line ports including S port, W port, P port and C port, and a built-in quantitative loop which setup with a bypass-slow path 52 and a quantitative flow path 51 with three fixed volume of 4 nL, 10 nL and 20 nL, and this can achieve nano-liter quantitative sample injection. Comply with the rotation of the built-in quantitative loop, the bypass-slow path 52 and the quantitative flow path 51 will switch between the S, W port and P, C port. To be specific, when the built-in quantitative loop at load position, the quantitative flow path 51 will connect the S port and W port, simultaneously the bypass-slow path 52 will connect P port and C port. When the built-in quantitative loop rotate 180 degrees and at inject liquid position, the bypass-slow path 52 will connect S port and W port, meanwhile the quantitative flow path 51 will connect P port and C port. The C port of the four-way sample injection valve 5 connects with the electrophoretic separation capillary 7 for conducting the quantitative sampling.

The four-way connector's 3 three ports are respectively connected to buffer syringe pump 1, shunt waste bottle 4 and the P port of the four-way sample injection valve 5. The described capillary pressure sensor 2 is set between the buffer syringe pump 1 and the four-way connector 3 which connected to the P port of the four-way sample injection valve 5 by a filter in the middle.

The automatic sampling flow path includes a six-channel liquid dispenser 13, a sampling needle 15, a sample tray 16, a cleaning tank 17, a buffer tube 14, a reagent bottle 20, a sampling flow pressure sensor 18, a syringe pump 19, a cleaning liquid bottle 21 and an autosampler waste bottle 22.

The six-channel liquid dispenser 13 has a fixed port and another six distributing ports which could switch to the fixed port, individually. The fixed port is connected to the buffer tube 14 and the six distributing ports are respectively connected to the sampling needle 15, one port of the four-way connector 3, S port of the four-way sample injection valve 5 and three reagent bottles 20 used for cleaning or balancing the electrophoretic separation capillary 7.

The syringe pump 19 is power source of the whole flow system and is equipped with a three dispensing valve as a switchover between functions of exhausting and cleaning. And the three valve ports of the three dispensing valve are respectively connected with the cleaning liquid bottle 21, the autosampler waste bottle 22 and the buffer tube 14. The sampling flow pressure sensor 18 is set between the three dispensing valve of the syringe pump 19 and the buffer tube 14, to detect the working pressure of sampling flow path.

The mentioned cleaning liquid bottle 21 contains cleaning liquid, usually select ethanol or deionized water, which is also the mobile phase of sample flow. The autosampler waste bottle 22, containing waste liquid of system cleaning, connects the W port of four-way sample injection valve 5. The cleaning tank 17 can simultaneously clean the internal and external and internal surface of the sample needle and connects the cleaning liquid bottle 21 with the autosampler waste bottle 22.

The buffer tube 14 has a certain quantitative function and it is the temporary storage place of some liquids such as sample, mobile phase, reagent and cleaning liquid. Two ends of the mentioned buffer tube 14 connect the six-channel liquid dispenser 13 and the syringe pump 19, and functions of system exhausting and balancing, auto-quantitative injection etc. can be accomplished through the cooperative work of this composite member.

The sample tray 16 with different sample bottles has cooling structure which could maintain a very low temperature and biological activity of enzymes and reduce the volatilization of samples. The sampling needle 15 has the function of puncture, can pierce through the rubber cap of sample bottle and reach into the sample solution. The sample needle 15 can be switched from the cleaning tank 17 to the sample tray 16.

All the functions of all the CE components can achieve the automation by computer program.

Figure 2:
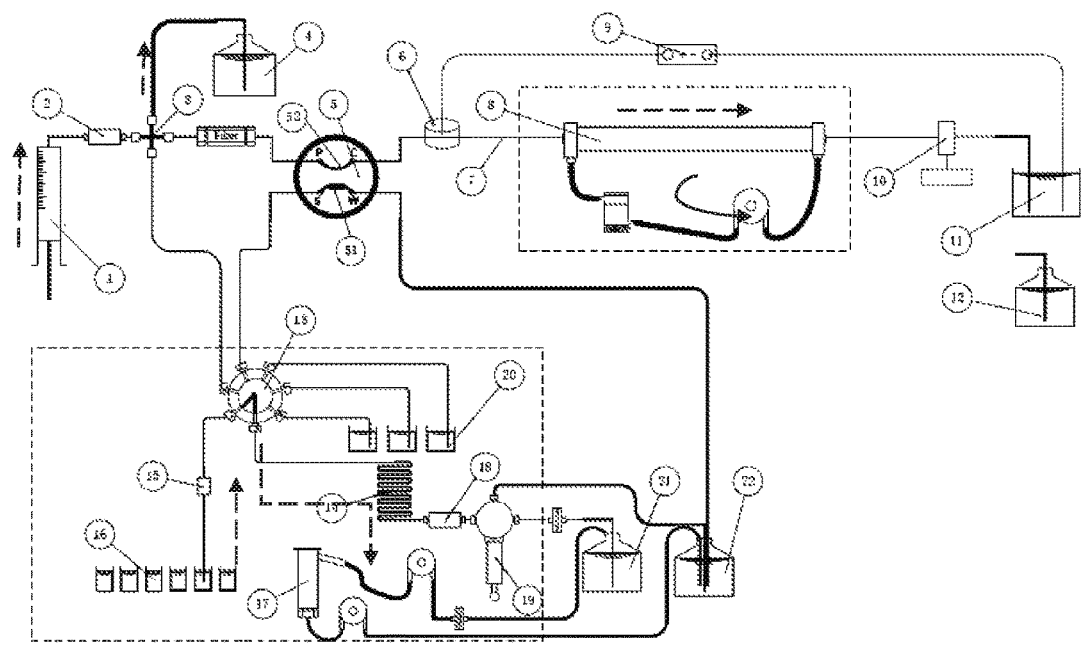
FIG. 2 is a first schematic of operating principle of this invention.

The operating principle of fully automated high-precision capillary electrophoresis instrument mentioned in the present invention is as following:

The first step, as shown in FIG. 2, when the outlet end of the described electrophoretic separation capillary 7 switch into the buffer solution outlet bottle 11, the four-way sample injection valve 5 will at load position, namely the quantitative flow path 51 of the four-way sample injection valve 5 has connected the A port and W port. The six-channel liquid dispenser 13 switch and feed through the sampling needle 15, and then the sampling needle 15 insert into a bottle of the sample tray 16. The syringe pump 19 indrafts the sample in the "displacement volume" usually equal to 1.5 times the volume of sampling prope 15 and brimming the sampling needle 15, meanwhile continue to indaft a certain amount of air so that the sample completely get into the buffer tube 14. At this moment, the internal surface of the sampling needle 15 has been washed by sample and the cleaning liquid and other interference components has been replaced so that these liquid would not get into the separating flow tube.

Figure 3:
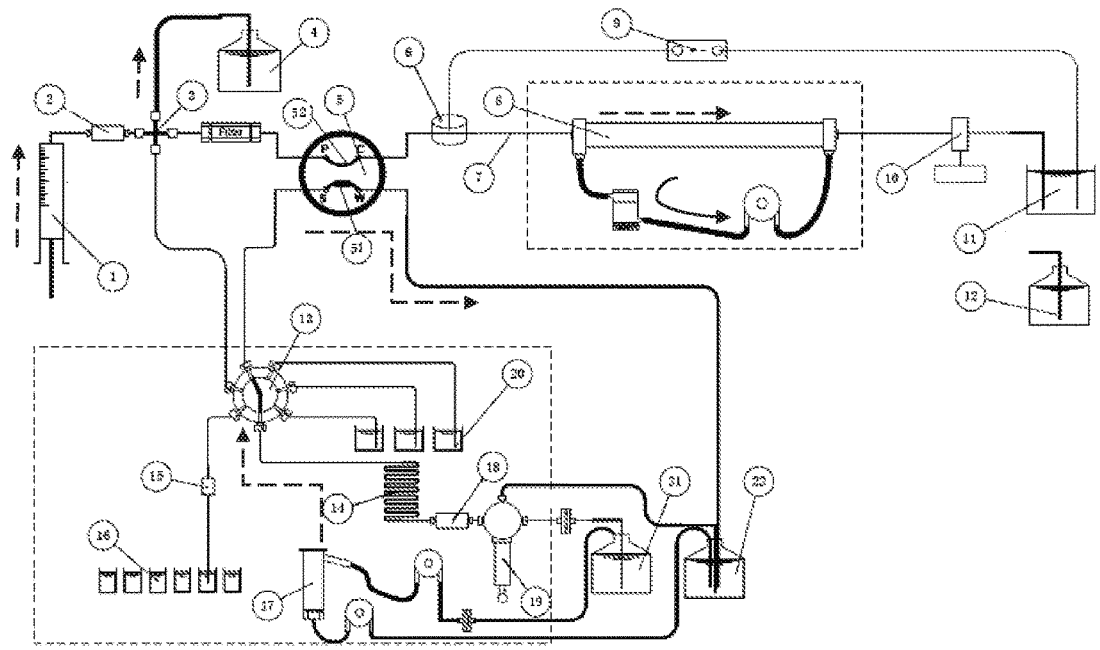
FIG. 3 is a second schematic of operating principle of this invention.

The second step, as shown in FIG. 3, the six-channel liquid dispenser 13 switch and connect the S port of the four-way sample injection valve 5 and the syringe pump 19 push "displacement volume" of sample into the built-in quantitative loop 5 and achieve quantitative by making the quantitative loop 51 full of sample. Meanwhile, the internal surface of the four-way sample injection valve 5 has been washed by sample and the cleaning liquid and other interference components has been replaced so that these liquid would not get into the separating flow tube.

Figure 4:
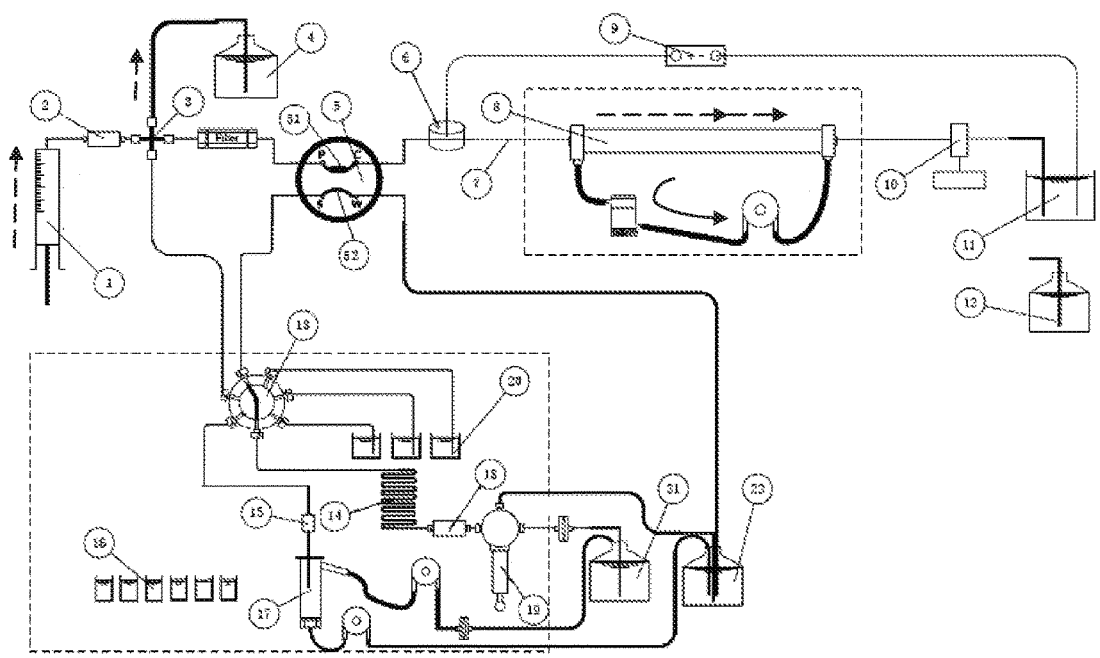
FIG. 4 is a third schematic of operating principle of this invention.

The third step, as shown in FIG. 4, the built-in quantitative loop rotates 180 degrees and the four-way sample injection valve 5 is at inject position, that is the quantitative flow path 51 full of sample in the four-way sample injection valve 5 connects P port and C port, and the sample in the loop flow into the electrophoretic separation capillary 7. The pressure from the buffer syringe pump 1 push the sample from the quantitative loop 51 into the electrophoretic separation capillary 7 and the quantitative electrophoresis analysis circle of samples start and meanwhile the sampling needle 15 move into the cleaning tank 17.

Figure 5:
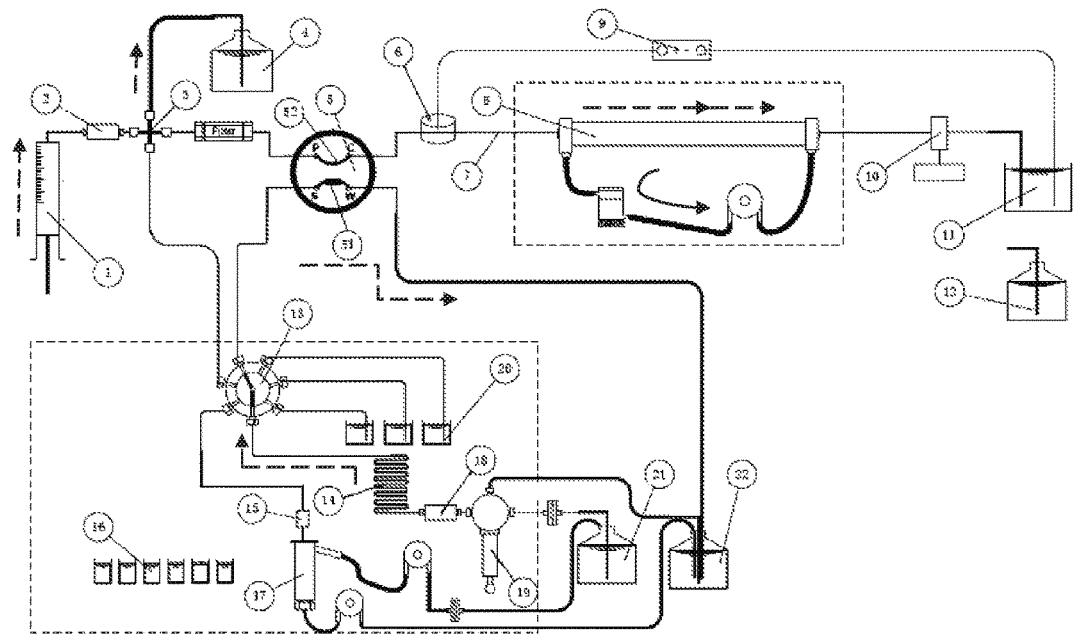
FIG. 5 is a forth schematic of operating principle of this invention.

The fourth step, as shown in FIG. 5, the built-in quantitative loop 51 rotate 180 degrees and the four-way sample injection valve 5 is at load position, that is the quantitative loop path 51 connects S port and W port. During the process of electrophoresis analysis, the six-channel liquid dispenser 13 maintain the connection with the S port of four-way sample injection valve 5, the syringe pump 19 push the cleaning liquid in the cleaning liquid bottle 21 into the four-way sample injection valve 5 so that the built-in quantitative loop could be washed at low flow rate.

Figure 6:
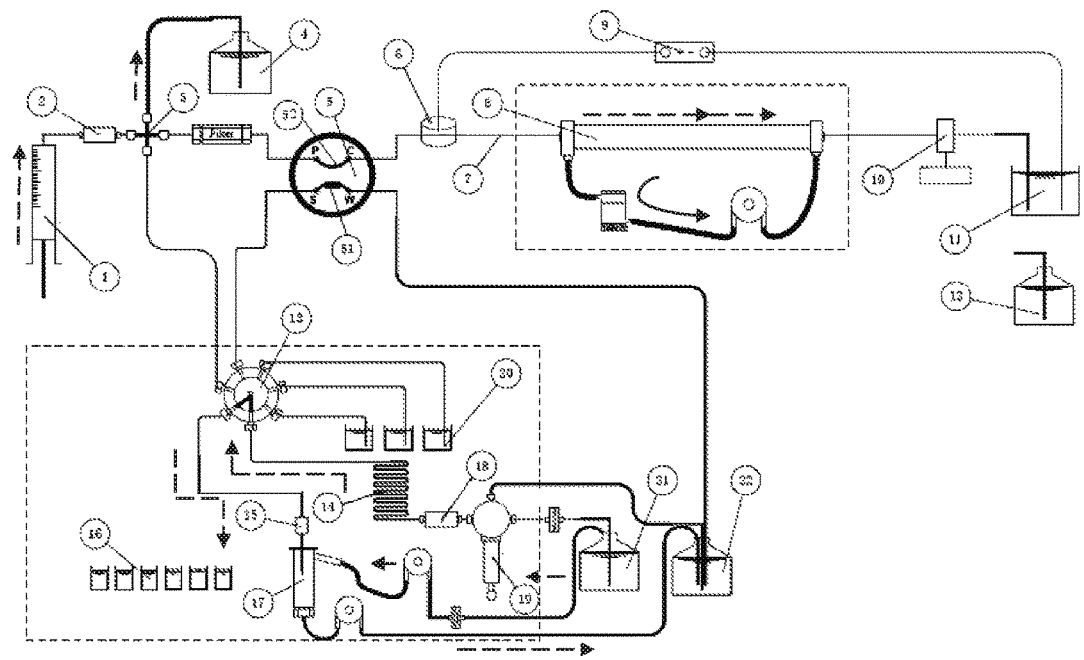
FIG. 6 is a fifth schematic of operating principle of this invention.

The fifth step, as shown in FIG. 6, during the process of electrophoresis analysis, the six-channel liquid dispenser 13 switch and connect the sampling needle 15 inserted into the cleaning bottle 17. And the syringe pump 19 push the cleaning liquid into the sampling needle 15, so that the sampling needle 15 and its flow tube could be washed.

Figure 7:
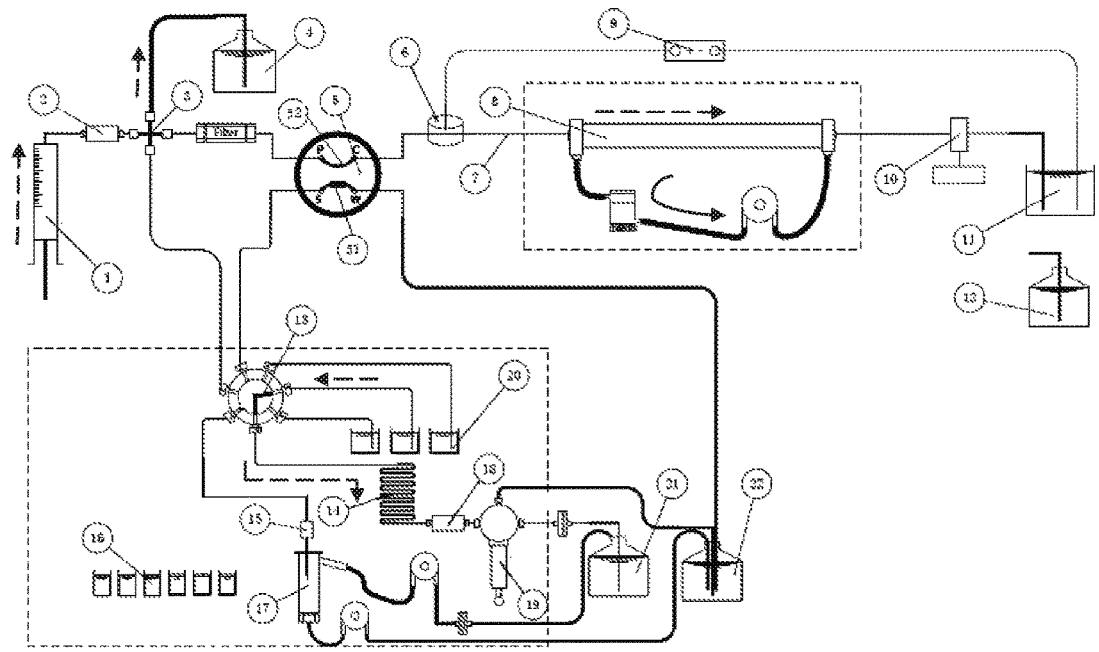
FIG. 7 is a sixth schematic of operating principle of this invention.

The sixth step, as shown in FIG. 7, after the electrophoresis analysis, entered the stage of reagent cleaning and balancing the electrophoretic separation capillary 7. The six-channel liquid dispenser 13 switch and connect the reagent bottle 21, and the syringe pump 19 indraft the reagent used for cleaning and balancing electrophoretic separation capillary 7 into the buffer tube 14.

Figure 8:
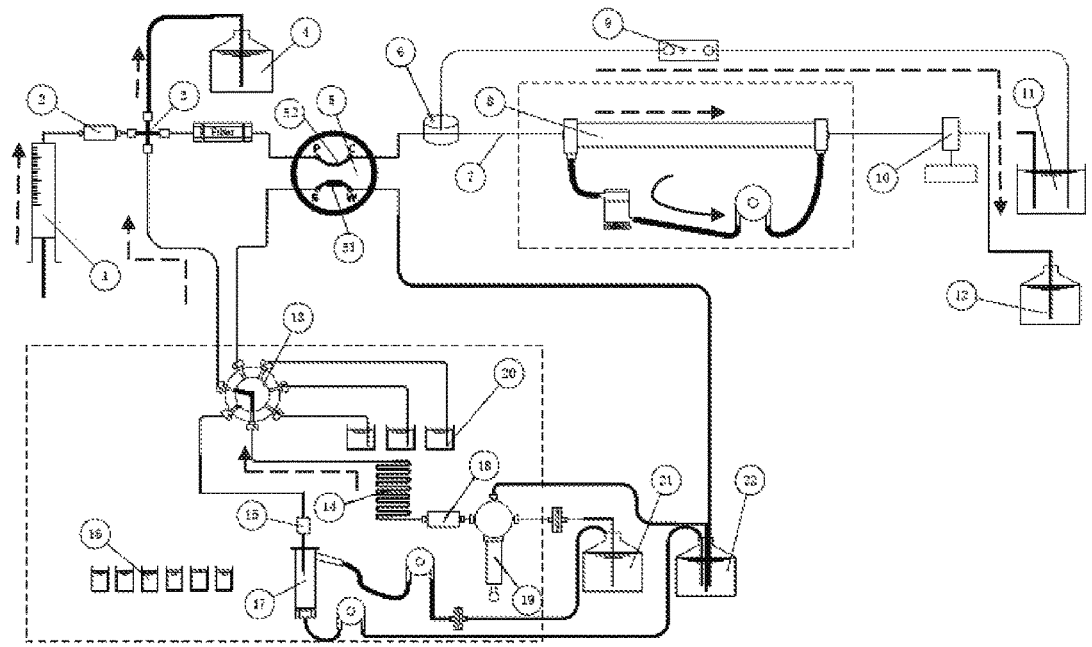
FIG. 8 is a seventh schematic of operating principle of this invention.

The seventh step, as shown in FIG. 8, the outlet end of the electrophoretic separation capillary 7 switches and connects the balance waste liquid bottle 12, and the six-channel liquid dispenser 13 switch and connect the four-way connector 3, and then the syringe pump 19 push the reagent in buffer tube 14 into the electrophoretic separation capillary 7 through the bypass-slow path 52 of four-way sample injection valve 5 at a specific speed. This can clean and balance the electrophoretic separation capillary 7 and the waste liquid after washing get into the balance waste liquid bottle 12.

The eighth step, as shown in FIG. 8., the six-channel liquid dispenser 13 maintain the connection with the four-way connector 3, and the cleaning liquid in the cleaning liquid bottle 21 should be push into the buffer tube 14 by the syringe pump 19, and then get into the electrophoretic separation capillary 7, which could clean the whole buffer tube 14 and the electrophoretic separation capillary 7.

The fully automated high-precision capillary electrophoresis instrument will restore the original state after cleaning and can start a new round of electrophoretic analysis from the first step.

In the course of their work, the functions of all the capillary electrophoresis instrument components can achieve the automation by computer program.

The claimed scope of the present invention is not limited to the embodiments described above, but also should include other obvious changes and alternatives.

What is claimed is:

1. A fully automated high-precision capillary electrophoresis instrument, comprising an electrophoresis system, the electrophoresis system comprising an electrophoretic separation capillary with its outlet inserting in a buffer solution bottle and a column thermostat and an detector being successively connected on the electrophoretic separation capillary, a high-voltage power supply with one electrode inserting into the buffer solution bottle and the other electrode connecting to the electrophoretic separation capillary through an electrical electric decoupler and forming a high-voltage electric field across the electrophoretic separation capillary, characterized by:
the capillary electrophoresis instrument further comprising a sample injection flow path connected with the electrophoresis system and an automatic sampling flow path connected with the sample injection flow path;
the sample injection flow path comprising a shunt waste bottle, a four-way sample injection valve and a buffer syringe pump respectively connected with three ports of a four-way connector;
the four-way sample injection valve, which is used for quantitatively injecting sample into the electrophoretic separation capillary, comprising four fixed ports, namely, an S port, a W port, a P port and a C port, and also comprising a rotatable built-in quantitative loop, wherein the C port is connected with the electrophoretic separation capillary, the P port is connected with the four-way connector, the built-in quantitative loop is provided with a bypass flow path and a quantitative flow path having a constant volume; as the built-in quantitative loop rotates, the bypass flow path and the quantitative flow path switch between connecting the S port and the W port and connecting the P port and the C port;
the automatic sampling flow path comprising a sampling needle, cleaning liquid bottle, reagent bottle as well as a six-channel liquid dispenser and a syringe pump which are connected by two ends of a buffer tube;
the syringe pump being provided with a three dispensing valve as a switchover between functions of exhausting and cleaning, and the three dispensing valve are respectively connected with the cleaning liquid bottle, an autosampler waste bottle and the buffer tube;
the six-channel liquid dispenser being provided with a fixed port and six dispensing ports which can be connected alternately with the fixed port, the fixed port being connected with the buffer tube, and the six distributing ports being respectively connected with the sampling needle, one port of the four-way connector, the S port of the four-way sample injection valve and three reagent bottles with different reagents for cleaning and balancing the electrophoretic capillary;
a cleaning tank for cleaning the sampling needle being disposed between the cleaning liquid bottle and the autosampler waste bottle, the sampling needle switching to inset into the cleaning tank and the sample tray with different samples;
the autosampler waste bottle being connected to the W port of the four-way sample injection valve.

2. The fully automated high-precision capillary electrophoresis instrument of claim 1, wherein the electrophoresis system comprises a balance waste liquid bottle, the outlet of electrophoretic separation capillary can switch connect to the balance waste liquid bottle and the buffer solution outlet bottle.

3. The fully automated high-precision capillary electrophoresis instrument of claim 1, wherein a quantitative path of the four-way sample injection valve has volume between 1 nL to 20 nL.

4. The fully automated high-precision capillary electrophoresis instrument of claim 1, wherein a capillary pressure sensor is provided to connect the buffer syringe pump and the four-way connector for detecting a working pressure of tubes, and a sampling flow pressure sensor is provided between the three dispensing valve of the syringe pump and the buffer tube for detecting a working pressure of sampling flow path.

5. The fully automated high-precision capillary electrophoresis instrument of claim 1, wherein the sample tray has a constant temperature structure and a cooling structure.

6. The fully automated high-precision capillary electrophoresis instrument of claim 1, wherein the cleaning liquid bottle contains cleaning liquid, and the cleaning liquid is ethanol or deionized water.

7. The fully automated high-precision capillary electrophoresis instrument of claim 1, wherein the functions of all the capillary electrophoresis components achieve the automation by a computer program.

8. The fully automated high-precision capillary electrophoresis instrument of claim 1, wherein the four-way connector and shunt waste bottle were connected with a shunt tube, which can balance the internal pressure of capillary electrophoresis.

9. The fully automated high-precision capillary electrophoresis instrument of claim 1, wherein the detector should be UV detector on the columns or other kinds of detectors on the columns.

10. The fully automated high-precision capillary electrophoresis instrument of claim 2, wherein a quantitative path of the four-way sample injection valve has volume between 1 nL to 20 nL.

* * * * *